(12) United States Patent
Sournac et al.

(10) Patent No.: US 10,143,495 B2
(45) Date of Patent: Dec. 4, 2018

(54) VERTEBRAL OSTEOSYNTHESIS EQUIPMENT

(71) Applicant: Medicrea International, Rillieux la Pape (FR)

(72) Inventors: Denys Sournac, Reyrieux (FR); Thomas Mosnier, Rochetaillee sur Saone (FR); David Ryan, Collonges au Mont d'or (FR)

(73) Assignee: Medicrea International, Rillieux la Pape (FR)

( * ) Notice: Subject to any disclaimer, the term of this patent is extended or adjusted under 35 U.S.C. 154(b) by 0 days.

(21) Appl. No.: 15/447,434

(22) PCT Filed: Oct. 12, 2015

(86) PCT No.: PCT/IB2015/057785
§ 371 (c)(1),
(2) Date: Mar. 2, 2017

(87) PCT Pub. No.: WO2016/059532
PCT Pub. Date: Apr. 21, 2016

(65) Prior Publication Data
US 2017/0209180 A1    Jul. 27, 2017

(30) Foreign Application Priority Data
Oct. 15, 2014  (FR) .................................... 14 59907

(51) Int. Cl.
*A61B 17/70*    (2006.01)

(52) U.S. Cl.
CPC ...... *A61B 17/7011* (2013.01); *A61B 17/7007* (2013.01); *A61B 17/7008* (2013.01); *A61B 17/7041* (2013.01)

(58) Field of Classification Search
CPC ............ A61B 17/7011; A61B 17/7008; A61B 17/7041
USPC .......................... 606/259–261, 264, 265, 278
See application file for complete search history.

(56) References Cited

U.S. PATENT DOCUMENTS

| | | | |
|---|---|---|---|
| 5,613,968 A * | 3/1997 | Lin ..................... | A61B 17/7001 411/389 |
| 6,749,613 B1 | 6/2004 | Pasquet | |
| 7,862,593 B2 * | 1/2011 | Clement ............ | A61B 17/7037 606/250 |
| 2008/0312692 A1 | 12/2008 | Brennan et al. | |
| 2009/0062859 A1 * | 3/2009 | Mahoney ........... | A61B 17/1757 606/278 |
| 2011/0307013 A1 | 12/2011 | Winslow et al. | |
| 2012/0209332 A1 * | 8/2012 | Janowski ........... | A61B 17/7038 606/278 |

* cited by examiner

*Primary Examiner* — Pedro Philogene
*Assistant Examiner* — David C Comstock
(74) *Attorney, Agent, or Firm* — M&B IP Analysts, LLC.

(57) ABSTRACT

Vertebral osteosynthesis equipment is presented. The equipment includes at least one connecting bar having an assembly portion, at least two anchoring members and at least one connecting part of the so-called "side loading" type; the assembly portion includes at least one protruding lug situated on the side of one of its ends, and the connecting part has a longitudinal slot emerging in said engagement duct, sized to receive said lug in an adjusted manner, but with the lug being able to slide therein, said connecting part being able to be engaged on said assembly portion beyond that lug.

11 Claims, 3 Drawing Sheets

VERTEBRAL OSTEOSYNTHESIS EQUIPMENT

BACKGROUND

The present invention relates to a vertebral osteosynthesis equipment.

To treat the degeneration of one or more vertebral joints, it is known to use vertebral osteosynthesis equipment comprising anchoring members for anchoring to the vertebrae (pedicle screws and/or laminar hooks), connecting bars, connecting parts for connecting said bars to said anchoring members, and tightening nuts for tightening said connecting parts relative to said bars and anchoring members. As an example, patent application publication no. WO 98/55038 describes such an equipment.

In general, the existing equipment does not always appear to be well-suited to treating a short vertebral column segment, i.e., resolving a degeneration at one or two vertebral joints. In particular, they are relatively complicated and time-consuming to implant, which noticeably extends the procedure time.

Such an equipment may comprise at least one connecting part of the so-called "side loading" type, like those described in the aforementioned patent application publication no. WO 98/55038, i.e., in which the duct for engaging the connecting bar is laterally offset relative to a duct allowing the part to be mounted on a proximal pin comprised by the associated anchoring member. An equipment of this type has the drawback of causing, particularly when the connecting bar is short, the risk of one or more connecting parts escaping from that bar.

Furthermore, this type of equipment has the drawback of not ruling out pivoting of the connecting bar relative to the anchoring members during tightening of the nuts, occurring even more when that bar is short and curved. This may result in defective angular positioning of the bar, leading to an imperfect or even defective correction of the treated segment, and therefore involving loosening of the nuts and repositioning of the bar.

A vertebral osteosynthesis equipment also comprises at least one connecting part of the so-called "top loading" or "tulip" type, i.e., forming an engagement duct of the connecting bar whose axis is secant to the axis of the vertebral anchoring screw, said duct being closed, after implantation of the connecting bar thereon, by a threaded stopper screwed into the "tulip". This type of equipment has the drawback of making it possible for the connecting bar to pivot as cited above, which occurs even more when that bar is short and curved. The threaded stoppers can be difficult to place, in particular because the connecting bar may not always be completely engaged in the ducts formed by the "tulips", and it is then necessary to use an instrument to push the connecting bar into those duct so that it is possible to place the stoppers. Furthermore, such stoppers have small sizes and may undergo a deterioration of their thread when they are placed, problem known as "cross threading".

The present invention aims to provide a vertebral osteosynthesis equipment resolving all of these drawbacks.

Furthermore, patent application publication no. U.S. 2008/312692 A1 describes a vertebral osteosynthesis equipment comprising at least one connecting bar, at least two anchoring members and at least one connecting part for connecting the connecting bar to the anchoring members. The connecting part comprises an engagement duct of the bar that is laterally offset relative to an assembly duct on the corresponding anchoring member. In this equipment, the part of the connecting bar designed to be engaged in said engagement duct is smooth, which does not make it possible to resolve the aforementioned drawback of the risk of one or more connecting parts escaping outside the bar, particularly when the connecting bar is short.

The main aim of the invention is therefore to provide simple and easy-to-place equipment that is particularly well-suited to treating a short vertebral column segment.

Another aim of the invention is to provide an equipment in which the risk of a connecting part of the so-called "side loading" type escaping outside the connecting bar is eliminated.

An additional aim of the invention is to provide an equipment in which the risk of pivoting of the connecting bar relative to the connecting parts is eliminated.

Still another aim of the invention is to provide an equipment in which the assembly of the connecting bar to the anchoring members is done simply and quickly.

SUMMARY

This equipment comprises:
- at least one connecting bar having an assembly portion designed to extend along the vertebrae be treated, this assembly portion having a circular cross-section;
- at least two anchoring members designed to be anchored in the vertebrae be treated, each anchoring member comprising a threaded proximal pin;
- at least one connecting part of the so-called "side loading" type, i.e., comprising an engagement duct for the engagement of said assembly portion that is laterally offset relative to an assembly duct for the engagement of the connecting part on the proximal pin comprised by the associated anchoring member; said engagement duct has a circular cross-section and said assembly portion is designed to be engaged through said engagement duct, the connecting part being capable to pivot around said assembly portion when the assembly portion is engaged in the engagement duct; and
- tightening nuts designed to be screwed on said threaded proximal pins of the anchoring members, so as to mount said connecting part (4) on said associated anchoring member.
- said assembly portion comprises at least one protruding lug situated on the side of one of its ends, and
- said connecting part has a longitudinal slot emerging in said engagement duct, sized to receive said lug in an adjusted manner, but with the lug being able to slide therein, said connecting part being able to be engaged on said assembly portion beyond that lug.

Once said connecting part is engaged past that lug, the connecting part can pivot relative to said assembly portion; it can then only be removed from the assembly portion in the angular position allowing it to be engaged on the lug. This connecting part is thus made "captive" relative to the connecting bar, such that the risk of the connecting part escaping from said assembly portion is made very low.

Preferably,
- said engagement duct is arranged on one side of the connecting part, so that, when the connecting part is engaged on said assembly portion, the connecting part adopts by gravity a first angular position on the assembly portion;
- the lug and said slot are so positioned relative to, respectively, the connecting bar and the connecting part that the angular engagement position permitting to engage the connecting part on the lug is a second angular position distinct from said first angular position and angularly separated therefrom.

The connecting part adopts by gravity said first angular position when it is engaged on said assembly portion and has to be pivoted to said second angular position to be removed from said assembly portion, and is thus normally retained on said assembly portion during the implantation procedure.

Preferably, said first and second position are angularly separated by at least 90 degrees, and more preferably by 180 degrees.

Preferably, said connecting part is U-shaped, i.e., comprises a base part and two parallel branches connected to that base part, which are separated from one another by an interstice, said engagement duct of the assembly portion being defined by that base part and by the base of those parallel branches; and said longitudinal slot is formed by the portion of said interstice extending along the base of the parallel branches.

With this type of connection, it is thus not necessary to specifically arrange a slot able to allow the engagement of the connecting part on the lug: it is the part of the interstice bordering the engagement duct of the connecting bar that forms that slot.

According to another aspect of the invention, the connecting bar has an eyelet at one end and an intermediate portion connecting that eyelet to said assembly portion, said intermediate portion being dimensioned to laterally offset the axis of the eyelet relative to the longitudinal direction of said assembly portion, by a distance substantially equal to the distance by which, on said connection portion, said engagement duct of the assembly portion is offset relative to said assembly duct.

During the implantation of the equipment, the eyelet is directly engaged on the proximal pin of the anchoring member associated with it and said connecting part, engaged on said assembly portion, is engaged on the proximal pin of the anchoring member associated with it. The eyelet makes it possible, by comparison with a traditional equipment, to eliminate the need for an additional connecting part that would be situated close to one end of the bar and would therefore tend to escape from the bar during the implantation of the equipment; said intermediate portion makes it possible, notwithstanding this assembly using this eyelet, for said assembly portion to be positioned with its longitudinal direction substantially parallel to the longitudinal direction of the vertebral column, in order to immobilize the vertebrae, or correct the position of those vertebrae, in an adapted manner.

Said intermediate portion could be at a right angle relative to said assembly portion; it is, however, advantageously bent so as to be relatively compact with respect to the surrounding anatomical structures.

Preferably, said connecting bar comprises, at the connecting zone of said intermediate portion to said assembly portion, or near that zone, a bearing surface for an instrument making it possible to move said connecting part, engaged on said assembly portion.

This instrument thus makes it possible to move one anchoring member relative to the other so as to correct the position of two treated vertebrae, in which these anchoring members are implanted.

Said bearing surface is advantageously in the form of a collar secured to the connecting bar.

Such a collar offers a possibility of bearing over its entire perimeter.

Said assembly portion can be dimensioned lengthwise so as to receive two anchoring member/connecting part assemblies; the equipment then comprises not only a first assembly formed by said connecting part and said anchoring member associated with the connecting part, but also a second assembly formed by a second connecting part and a second anchoring member associated with that second connecting part.

According to one possibility, in that case, said second connecting part is of the "open" type, i.e., forms a curved portion that defines an engagement duct for the engagement of said assembly portion, said curved portion being able to surround the assembly portion only partially, and said second assembly comprises a closing means making it possible to close this engagement duct when said second connecting part is gripped on said associated second anchoring member.

This closing means may be made up of a step present on the anchoring member, as for example described by patent application publication No. WO 94/15554, or by a step present on the tightening nut, as for example described by patent application publication No. EP 0,441,084.

This closing means may be also be in the form of a locking part forming a passage through it, that passage allowing the engagement of that locking part on a threaded proximal pin comprised by said associated second anchoring member; said second connecting part then comprises:

a body forming said curved portion, and said locking part, which comprises:

a locking portion designed to bear against said associated second anchoring member and forming a lateral closing extension of said engagement duct, and an assembly portion dimensioned to be engaged in an assembly duct comprised by said body and to slide in said duct, that sliding occurring between a separated position of said body and said second connecting part, in which said lateral extension does not hinder the transverse engagement of said assembly portion in said engagement duct, and a close position of said body and said locking part, in which said lateral extension is at a distance from said curved portion such that it closes said engagement duct and it keeps said assembly portion in that duct.

The invention will be well understood, and other features and advantages thereof will appear, in reference to the appended diagrammatic drawing, showing, as a non-limiting example, one preferred embodiment of the equipment in question.

DESCRIPTION OF THE PREFERRED EMBODIMENTS

Figure 1:
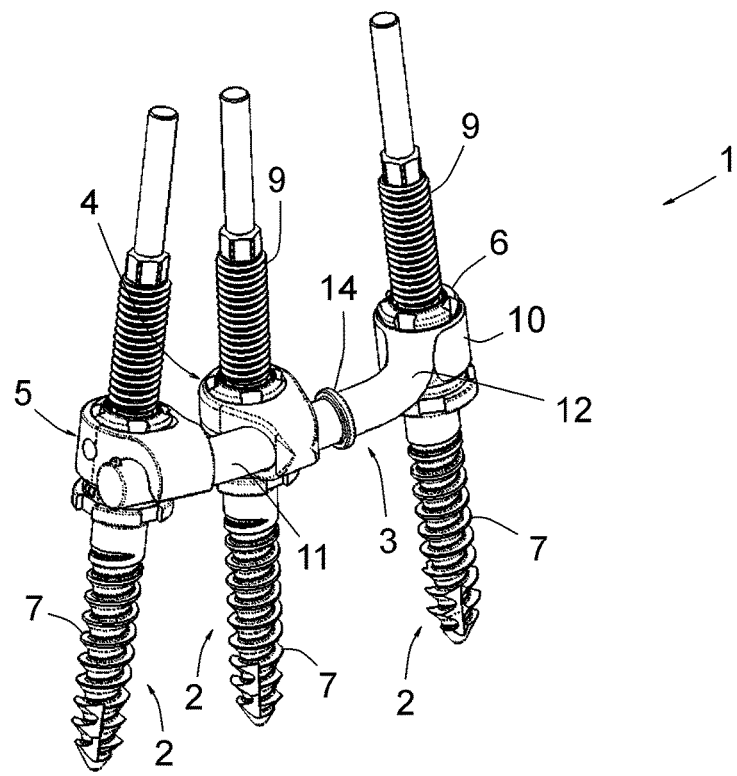
FIG. 1 is a perspective view of this equipment.
Figure 2:
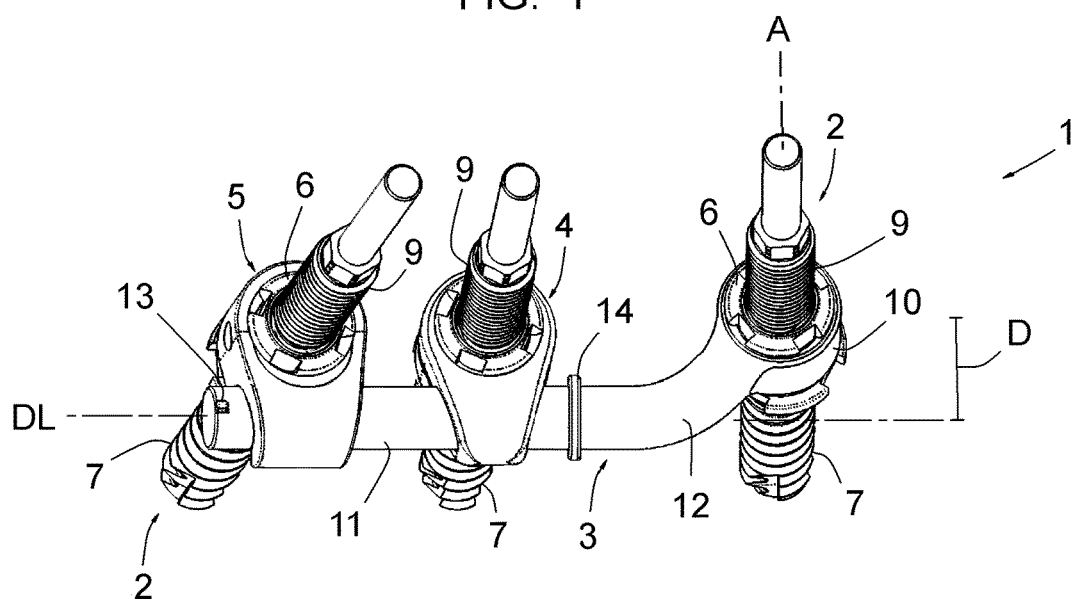
FIG. 2 is a slightly enlarged perspective view from another angle.

FIGS. 1 and 2 show a vertebral osteosynthesis equipment 1 comprising three anchoring members 2, a connecting bar 3, two connecting parts 4, 5 and tightening nuts 6.

The anchoring members 2 are of the well-known "polyaxial" type, in particular described in patent application publication No. WO 98/55038. Each of them therefore comprises a screw body 7, a proximal wall 8 (cf. FIGS. 8 and 9) forming a bearing surface for a connecting part 4 or 5 or for the eyelet 10 described below, and an articulated proximal pin 9, part of which is threaded and is able to receive a nut 6.

Figure 3:
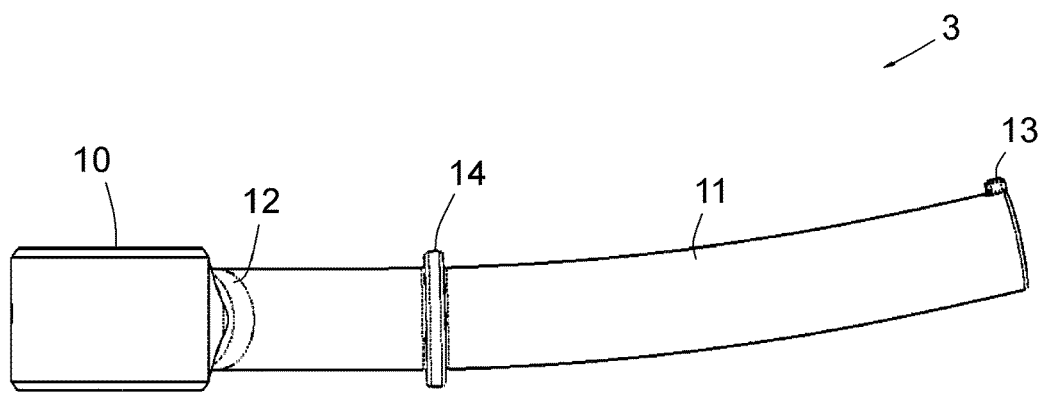
FIG. 3 is a side view of a connecting bar comprised by the equipment.
Figure 4:
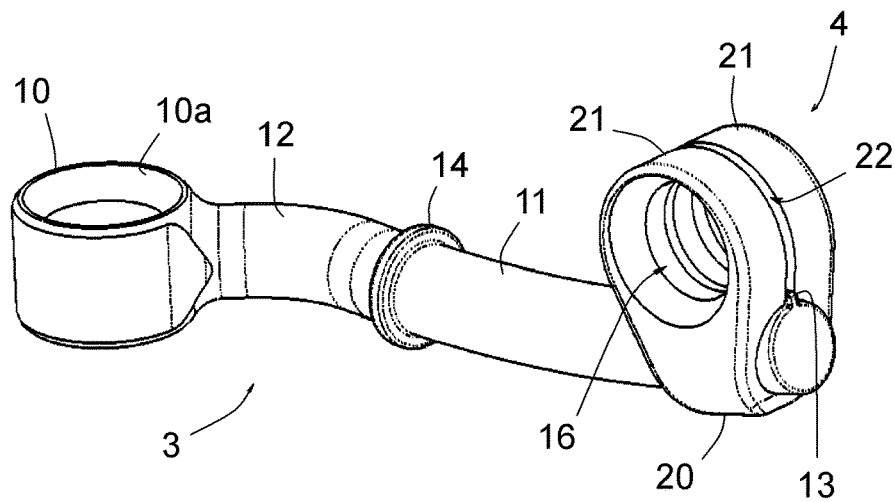
FIG. 4 is a perspective view of this connecting bar and a connecting part also comprised by the equipment.

The connecting bar 3 is more particularly visible in FIGS. 3 and 4. It comprises an eyelet 10 at one end, an assembly portion 11, also called "correction" portion, an intermediate bent portion 12 between the eyelet 10 and the assembly portion 11, a lug 13 and a collar 14.

The eyelet 10 is designed to be engaged on the pin 9 by an anchoring member 2, as shown in FIGS. 1 and 2, until it rests against said proximal bearing wall 8 thereof, and has a countersink 10a on its upper side, suitable for receiving a nut 6.

The assembly portion 11 is slightly bent, as shown in FIGS. 3 and 4, and is designed to receive the connecting parts 4 and 5. These parts are of the so-called "side loading" type, i.e., they each comprise, as shown in FIGS. 4 to 7, a duct 15 for engaging the assembly portion 11 that is laterally offset relative to an assembly duct 16 allowing the assembly of the connecting part 4, 5 on the proximal pin 9 comprised by the associated anchoring member 2.

The assembly portion 11 has a circular cross-section and the duct 15 of the connecting part 4 also has a circular cross-section, adjusted to the cross-section of the assembly portion 11, such that the connecting part 4 is capable to pivot around said assembly portion 11 when the assembly portion 11 is engaged in the duct 15.

Figure 5:
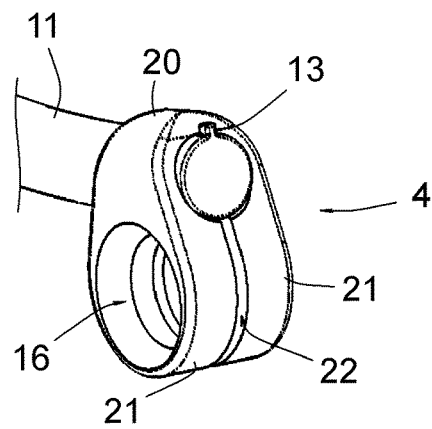
FIG. 5 is a partial view of the connecting bar, similar to FIG. 4, in a position different from the connecting part relative to the connecting bar.
Figure 6:
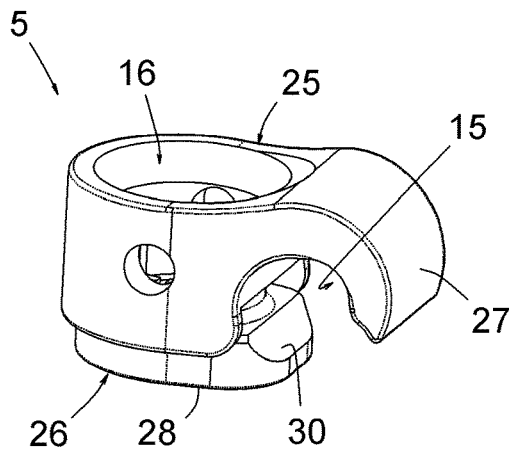
FIG. 6 is a perspective view of a second connecting part comprised by the equipment.
Figure 7:
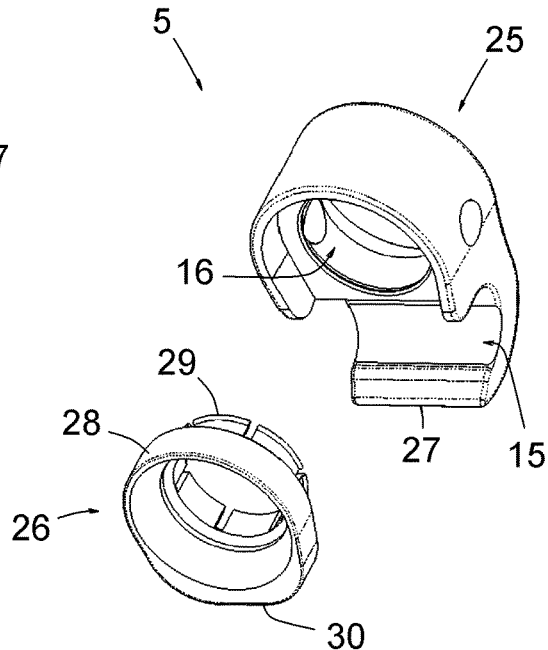
FIG. 7 is a perspective view of this second connecting part, from another angle and in exploded view.

Additionally, the duct 15 of the connecting part 4 is arranged on one side of the connecting part 4, so that, when the connecting part 4 is engaged on said assembly portion 11, the connecting part 4 adopts by gravity a first angular position on the assembly portion 11, shown on FIG. 5.

As particularly shown in FIG. 2, the intermediate portion 12 is bent so as to laterally offset the axis A of the eyelet 10 relative to the general longitudinal direction DL of the assembly portion 11, by a distance D substantially equal to the distance by which, on the connecting parts 4, 5, the axis of the engagement duct 15 is offset relative to the axis of the assembly duct 16. In this way, when the equipment 1 is assembled as shown in FIG. 2, the three anchor members 2 are substantially aligned parallel to the longitudinal direction DL and after implantation, the connecting bar 3 is positioned substantially parallel to the axis of the treated vertebral segment.

The lug 13 is situated at the end of the assembly portion 11 opposite the intermediate portion 12 and protrudes radially from the wall of that portion 11. It has a small width (i.e., its dimension in the direction DL), such that the connecting part 4 can be engaged on the portion 11 past it or beyond it, and has a thickness (i.e., its dimension perpendicular to the direction DL) such that it can be slidingly engaged in an interstice 22, or slot, formed by the connecting part 4, as described later.

The lug 13 and said interstice or slot 22 are so positioned relative to, respectively, the connecting bar 3 and the connecting part 4 that the angular engagement position permitting to engage the connecting part 4 on the lug 13 is a second angular position, shown on FIG. 4, distinct from said first angular position and angularly separated therefrom by 180 degrees.

The collar 14 is situated at the connecting zone of the intermediate portion 12 to the assembly portion 11. It forms a bearing surface for an instrument (not shown) making it possible to move the connecting part 4 engaged on the portion 11 relative to the eyelet 10. This instrument, known in principle, comprises a branch able to bear against the connecting part 4, and another branch, movable relative to the first branch, able to bear against the eyelet 10.

As particularly shown in FIGS. 4 and 5, the connecting part 4 is U-shaped, i.e., it comprises a base 20 and two parallel branches 21 connected to that base part, which are separated from one another by said interstice or slot 22. The engagement duct 15 of the portion 11 is defined by that base part 20 and by the base of these parallel branches 21.

As will be understood in reference to FIGS. 4 and 5, the part 4 is able to be engaged on the portion 11 by engagement of the interstice 22 on the lug 13, which requires that part 4 to be manually positioned as shown in FIG. 4. The part 4 is engaged on the portion 11 beyond the lug 13, which makes it possible for it to pivot relative to the portion 11 by gravity, until it assumes the position shown in FIG. 5, in which it is "captive" relative to the connecting bar 3. From that position, it can be brought to its engagement position on the pin 9 of the associated anchoring member 2 by simple pivoting around the portion 11.

The connecting part 5, more particularly visible in FIGS. 6 to 9, is formed by a body 25 and a locking part 26. It is of the "open" type, i.e., its body 25 forms a curved portion 27 defining said engagement duct 15, said curved portion 27 being able to only partially surround said assembly portion 11 engaged in that duct. Outside that portion 27, the body 25 defines the assembly duct 16.

The locking part 26 comprises a locking portion 28 and a central portion 29. The locking portion 28 is designed to bear against the proximal wall 8 of the associated anchoring member 2 and forms a lateral closing extension 30 of the engagement duct 15. The assembly portion 29 is in the form of a ring of teeth that are slightly radially flexible, which is dimensioned to be engaged with friction in the assembly duct 16. These teeth are able to slide with friction in this duct 16, between a separated position of the body 25 on the locking part 26, in which said lateral extension 30 does not hinder the transverse engagement of the assembly portion 11 in the engagement duct 15, and a close position of this body 25 and this locking part 26, in which said lateral extension 30 is at a distance from said curved portion 27 such that it contains the engagement duct 15 and retains the assembly portion 11 in that duct.

Figure 8:
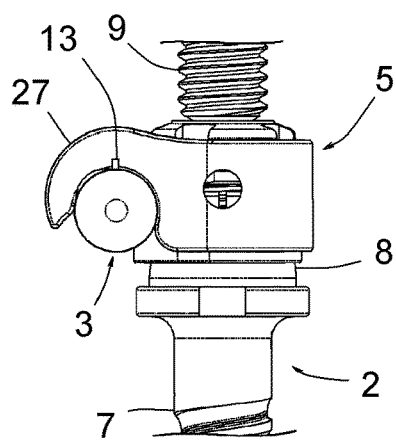
FIG. 8 is a side view of this second connecting part, assembled on a partially visible anchoring member, in one possible assembly position of the second connecting part on the anchoring member.
Figure 9:
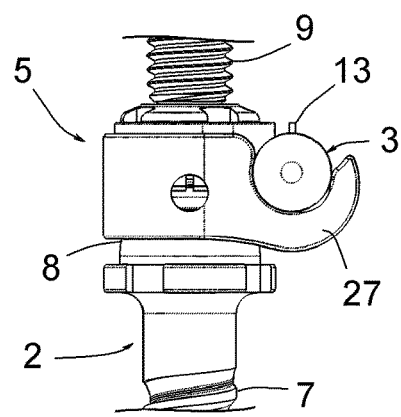
FIG. 9 is a view similar to FIG. 8, in another possible assembly position of the second connecting part on the anchoring member.

FIGS. 8 and 9 show that the part 5 can be placed on the anchoring member 2 with the opening of the duct 15 turned toward the screw body 7 (cf. FIG. 8) or with that opening turned toward the side opposite that screw body 7 (cf. FIG. 9).

In practice, during the implantation of the equipment 1, the eyelet 10 is engaged directly on the proximal pin 9 of the anchoring member 2 associated with it until it bears against the wall 8 of that member; at the same time, the connecting part 4, placed so as to be captive on the portion 11, is engaged on the proximal pin 9 of the anchoring member 2 associated with it. The eyelet 10 makes it possible, relative to a traditional equipment, to eliminate the need for an additional connecting part that would be situated near one end of the bar and would therefore be likely to escape from the bar during the implantation of the equipment; said intermediate portion 12 makes it possible, notwithstanding this assembly using this eyelet 10, for the assembled portion 11 to be positioned with its longitudinal direction DL substantially parallel to the longitudinal direction of the vertebral column, so as to immobilize the vertebrae, or correct the position of those vertebrae, appropriately.

The part 5 is used when the third anchoring member 2 is made necessary by the treatment to be performed. It is easy to engage, laterally, on the portion 11 due to the fact that it is of the "open" type, and the locking part 26 ensures perfect locking of that portion 11 in the duct 15 that it defines.

The various disclosed embodiments thus provides a vertebral osteosynthesis equipment having the decisive advantages of being quick and easy to place, and being particularly well-suited to the treatment of a short vertebral column segment, eliminating the risk of the connecting part 4 escaping from the connecting bar 3, eliminating the risk of pivoting of the connecting part 3 relative to the connecting parts 4 and 5, and making it possible to assemble the connecting bar 3 to the anchoring members 2 quickly and easily.

What is claimed is:

1. Vertebral osteosynthesis equipment, comprising:
   at least one connecting bar having an assembly portion designed to extend along the vertebrae be treated, this assembly portion having a circular cross-section;
   at least two anchoring members designed to be anchored in the vertebrae be treated, each anchoring member comprising an outwardly threaded proximal pin;
   at least one connecting part of the so-called "side loading" type, i.e., comprising an engagement duct for the engagement of said assembly portion that is laterally offset relative to an assembly duct for the engagement of the connecting part on the proximal pin comprised by the associated anchoring member; said engagement duct has a circular cross-section with openings on two opposing sides, and said assembly portion is designed to be engaged through said engagement duct, the connecting part being capable to pivot around said assembly portion when the assembly portion is engaged in the engagement duct; and
   tightening nuts designed to be screwed on said threaded proximal pins of the anchoring members, so as to mount said connecting part on said associated anchoring member;
   said assembly portion comprises at least one protruding lug situated on the side of one of its ends, and
   said connecting part has a longitudinal slot emerging in said engagement duct, sized to receive said lug in an adjusted manner, but with the lug being able to slide therein, said connecting part being able to be engaged on said assembly portion beyond that lug.

2. Equipment according to claim 1, characterized in that:
   said engagement duct is arranged on one side of the connecting part, so that, when the connecting part is engaged on said assembly portion, the connecting part adopts by gravity a first angular position on the assembly portion;
   the lug and said slot are so positioned relative to, respectively, the connecting bar and the connecting part that the angular engagement position permitting to engage the connecting part on the lug is a second angular position distinct from said first angular position and angularly separated therefrom.

3. Equipment according to claim 2, characterized in that said first and second position are angularly separated by at least 90 degrees, and more preferably by 180 degrees.

4. Equipment according to claim 1, characterized in that:
   said connecting part is U-shaped, i.e., comprises a base part and two parallel branches connected to that base part, which are separated from one another by an interstice, said engagement duct of the assembly portion being defined by that base part and by the base of those parallel branches; and
   said longitudinal slot is formed by the portion of said interstice extending along the base of the parallel branches.

5. Equipment according to claim 1, characterized in that the connecting bar has an eyelet at one end and an intermediate portion connecting that eyelet to said assembly portion, said intermediate portion being dimensioned to laterally offset the axis of the eyelet relative to the longitudinal direction of said assembly portion, by a distance substantially equal to the distance by which, on said connection portion, said engagement duct of the assembly portion is offset relative to said assembly duct.

6. Equipment according to claim 5, characterized in that said intermediate portion is at an angle.

7. Equipment according to claim 5, characterized in that said connecting bar comprises, at the connecting zone of said intermediate portion to said assembly portion, or near that zone, a bearing surface for an instrument making it possible to move said connecting part, engaged on said assembly portion.

8. Equipment according to claim 7, characterized in that said bearing surface is in the form of a collar secured to the connecting bar.

9. Equipment according to claim 1, characterized in that said assembly portion is dimensioned lengthwise so as to receive two anchoring members/connecting part assemblies; the equipment then comprises not only a first assembly formed by said connecting part and said anchoring member associated with the connecting part, but also a second assembly formed by a second connecting part and a second anchoring member associated with that second connecting part.

10. Equipment according to claim 9, characterized in that:
    said second connecting part is of the "open" type, i.e., forms a curved portion that defines said engagement duct of said assembly portion, said curved portion being able to surround the assembly portion only partially, and
    said second assembly comprises a closing means making it possible to close this engagement duct when said second connecting part is gripped on said associated second anchoring member.

11. Equipment according to claim 10, characterized in that said closing means may also be in the form of a locking part forming a passage through it, that passage allowing the engagement of that locking part on a threaded proximal pin comprised by said associated second anchoring member; said locking part then comprises:
    a body forming said curved portion, and
    said locking part, which comprises:

a locking portion designed to bear against said associated second anchoring member and forming a lateral closing extension of said engagement duct, and an assembly portion dimensioned to be engaged in an assembly duct comprised by said body and to slide in said duct, that sliding occurring between a separated position of said body and said locking part, in which said lateral extension does not hinder the transverse engagement of said assembly portion in said engagement duct, and a close position of said body and said locking part, in which said lateral extension is at a distance from said curved portion such that it closes said engagement duct and it keeps said assembly portion in that duct.

* * * * *